United States Patent [19]

Mehta et al.

[11] Patent Number: 5,191,103

[45] Date of Patent: Mar. 2, 1993

[54] PROCESS AND COMPOSITION FOR PROMOTING HYDROSILYLATION REACTIONS USING STERICALLY HINDERED NITROGEN-CONTAINING AND PHOSPHORUS-CONTAINING COMPOUNDS

[75] Inventors: Kunj R. Mehta, Parkersburg, W. Va.; James D. Reedy, Marietta, Ohio

[73] Assignee: Union Carbide Chemicals & Plastics Technology Corporation, Danbury, Conn.

[21] Appl. No.: 815,821

[22] Filed: Dec. 30, 1991

[51] Int. Cl.$^5$ .............................................. C07F 7/08
[52] U.S. Cl. .................... 556/479; 502/162; 502/167
[58] Field of Search ............... 556/479; 502/162, 167

[56] References Cited

U.S. PATENT DOCUMENTS

| | | | |
|---|---|---|---|
| 2,637,738 | 5/1953 | Wagner | 260/448.2 |
| 3,057,902 | 10/1962 | Pike | 556/479 |
| 3,159,601 | 12/1964 | Ashby | 260/46.5 |
| 3,220,972 | 11/1965 | Lamoreaux | 260/46.5 |
| 3,715,334 | 2/1973 | Karstedt | 260/46.5 UA |
| 3,795,656 | 3/1974 | Martin | 260/46.5 E |
| 3,925,434 | 12/1975 | Chuang | 260/448.2 E |
| 4,292,433 | 9/1981 | Koga et al. | 556/479 |
| 4,398,010 | 8/1983 | Adkins | 528/15 |
| 4,417,068 | 11/1983 | Kollmeier et al. | 556/479 |
| 4,417,069 | 11/1983 | Brown | 556/479 |
| 4,427,574 | 1/1984 | Pierpoint | 502/154 |
| 4,431,789 | 2/1984 | Okazaki et al. | 528/15 |
| 4,447,633 | 5/1984 | Boudjounk | 556/479 |
| 4,510,094 | 4/1985 | Drahnak | 260/429 |
| 4,578,497 | 3/1986 | Onopchenko et al. | 556/479 |
| 4,605,722 | 8/1986 | Suzuki | 528/15 |
| 4,614,812 | 9/1986 | Schilling, Jr. | 556/406 |
| 4,681,963 | 7/1987 | Lewis | 556/453 |
| 4,687,870 | 8/1987 | Cavezzan | 556/136 |
| 4,699,813 | 10/1987 | Cavezzan | 427/387 |
| 4,705,765 | 11/1987 | Lewis | 502/152 |
| 4,820,674 | 4/1989 | Shiozawa et al. | 502/169 |
| 5,084,591 | 1/1992 | Shinohara et al. | 556/479 |

OTHER PUBLICATIONS

Chemical Abstract 111: 78085m, Hu, C., et al., Studies on Hydrosilylation of Allyl Chloride Catalyzed by Chloroplatinic Acid-Amine Systems, 1989.
Chemical Abstract 109: 54927v, Michalska, Z. M., Transition Metal Complexes with Polystyrene-Attached Amine-Phosphine Ligands as Hydrosilylation Catalysts, 1988.
Chemical Abstract 107: 40049g, Iovel, I. G., et al., Quaternary Onium Hexachloroplatinates: Novel Hydrosilylation Catalysts, 1987.
J. W. Ryan, G. K. Menzie & J. L. Speier, J. Am. Chem. Soc., The Addition of Silicon Hydrides to Olefinic Double Bonds, Part V., The Addition of Allyl and Methallyl Chlorides, vol. 82, pp. 3601-3604, Jul. 20, 1960.
J. March, Advanced Organic Chemistry; Reactions, Mechanisms, and Structure-Third Edition, p. 689, 1988.
R. T. Morrison and R. N. Boyd, Organic Chemistry; Third Edition, Amines I. Preparation and Properties, Chapter 22, pp. 740-741, 1980.

*Primary Examiner*—Paul F. Shaver
*Attorney, Agent, or Firm*—W. F. Gray

[57] ABSTRACT

A process and a catalytic composition for carrying out a platinum catalyzed hydrosilylation reaction between an SiH-containing material and a terminal olefin. The process of the invention involves heating the reactants in the presence of a platinum catalyst and a promoter which is a hindered amine or phosphine, or acid salt thereof, the promoter containing at least 6 carbon atoms and having the formula

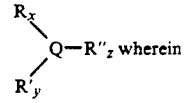

Q is N or P; when Q is N, R is H, alkyl of 1-18 carbon atoms, nonterminal alkenyl of 4-18 carbon atoms, arylalkyl of 7-25 carbon atoms, or a derivative thereof; when Q is P, R is alkyl of 1-18 carbon atoms, nonterminal alkenyl of 4-18 carbon atoms, arylalkyl of 7-25 carbon atoms, or a derivative thereof; x is 0 or 1; R' is alkyl of 1-18 carbon atoms, nonterminal alkenyl of 4-18 carbon atoms, arylalkyl of 7-25 carbon atoms, or a derivative thereof; y is 0, 1, or 2; R" is a branched group having a 2° or 3° carbon atom bonded directly to Q, and is alkyl of 3-18 carbon atoms, nonterminal alkenyl of 4-18 carbon atoms, arylalkyl of 7-25 carbon atoms, or a derivative thereof; z is 1, 2, or 3 and z=3-x-y; and two R' groups, two R" groups, or one R' and one R" may be taken together to constitute a divalent moiety forming a 5-7 membered ring containing a Q atom. The catalytic composition comprises a catalytically active platinum-containing material and a promoter as defined above.

10 Claims, No Drawings

PROCESS AND COMPOSITION FOR PROMOTING HYDROSILYLATION REACTIONS USING STERICALLY HINDERED NITROGEN-CONTAINING AND PHOSPHORUS-CONTAINING COMPOUNDS

FIELD OF THE INVENTION

This application relates to hydrosilylation reactions, and more particularly, to the use of sterically hindered amines and phosphines as promoters for platinum-catalyzed hydrosilylations of siloxanes and silanes.

BACKGROUND OF THE INVENTION

Hydrosilylation reactions involve the addition of an Si-H across a terminal olefinic double bond. They have been conducted historically using catalysts derived from chloroplatinic acid (CPA), although elemental platinum on various supports has also been used. These reactions typically suffer from side reactions such as dehydrocondensation, and in the case of certain polyethers, acetal formation.

Dehydrocondensation initially involves the reaction of a hydridosilicon compound and a hydroxyl-containing material such as an alcohol or water to yield hydrogen and an alkoxy silane or silanol. The alkoxy silane may form a crosslinked material in a subsequent reaction step, and the silanol may also subsequently form crosslinked material under the reaction conditions.

Acetal formation occurs when an allyl polyether starting material undergoes molecular rearrangement to a propenyl ether which reacts with alcohol present in the system.

Other difficulties which have been experienced in chloroplatinic acid catalyzed hydrosilylation reactions are: a requirement for relatively high platinum levels in the reactions, with the attendant expense; insufficiently high rates of hydrosilylation; a requirement for relatively high reaction temperatures, with the attendant risk of increasing objectionable side reactions; and objectionable selectivity of the hydrosilylation reaction, with some olefinic materials in the reaction mixtures reacting in preference to others.

Traditionally, polysiloxane-polyether copolymer surfactants have been prepared by a hydrosilylation reaction between a polysiloxane containing Si-H moieties and a terminally unsaturated polyether, in a solvent such as toluene or isopropanol. These solvents must ultimately be removed from the reaction product in the manufacturing process, leading to environmental and economic difficulties. The use of isopropanol also suffers from the additional difficulties that a buffer is required to prevent or reduce dehydrocondensation between Si-H moieties and the alcohol, relatively high platinum levels are required, and the hydrosilylation reactions do not always occur as rapidly as desired.

To avoid the above-discussed problems associated with the use of solvents in the hydrosilylation reaction for preparation of siloxane-polyether copolymers, it has been proposed to conduct the reaction under solventless conditions When this was first attempted, high yields of dehydrocondensation products and acetals were produced, ultimately giving extensive crosslinking. Addition of alkali metal carboxylate salts to the system controlled the dehydrocondensation and acetal-forming reactions, as shown in U.S. Pat. No. 4,847,398, but resulted in hydrosilylation reactions which in some cases exhibited objectionable selectivity, low reaction rates, and high platinum requirements.

In addition to polysiloxane-polyether copolymer surfactants, certain silane materials are also prepared via hydrosilylation reactions. Such reactions typically involve a silane material such as trichlorosilane or a trialkoxysilane, and an olefinically-unsaturated material such as allyl chloride. These reactions are sometimes hard to initiate, requiring high reaction temperatures which can produce reduced selectivity and objectionable increases in undesired byproducts of the reaction.

Certain amines have been employed in hydrosilylation reactions to control the dehydrocondensation and acetal-forming side reactions. These have been relatively simple nonhindered amines. In some cases they have had an inhibiting effect on the rate of the hydrosilylation reaction. The prior art has apparently not recognized the distinction between amines and phosphines which can act as bases toward proton donors and also act as general nucleophiles or ligands for the platinum catalyst, and the highly hindered amines and phosphines which cannot act as nucleophiles or ligands for the platinum catalyst Treatment of chldroplatinic acid with an aminofunctional silane or siloxane is described in U.S. Pat. No. 3,795,656. The resulting catalysts are described in U.S. Pat. No. 4,398,010 as being too slow to react for certain applications, and this patent further discloses reacting the initially formed ammonium-platinum complex with a compound having aliphatic unsaturation in the presence of a basic compound to form a platinum complex having improved hydrosilylation activity.

The use of compounds containing phosphorus, sulfur, nitrogen, or aliphatic unsaturation to suppress platinum catalyzed reaction of water or OH groups with excess SiH groups to generate hydrogen in cured addition-type silicone material is disclosed in U.S. Pat. No. 4,605,722. Some of these materials are considered inhibitors or poisons for general hydrosilylation reactions. Examples of nitrogen- and phosphorous-containing compounds employed by the reference are N,N-diethylaninoethanol, and triethylphosphine.

Ligands containing both phosphine and amine functionalities have been described for use with various transition metals for hydrosilylation of aliphatic olefins. See Chemical Abstracts 109: 54927v.

Hydrosilylation of allyl chloride with trichlorosilane catalyzed by platinum on charcoal or chloroplatinic acid gives substantial amounts of silicon tetrachloride and n-propyltrichlorosilane byproducts. See U.S. Pat. No. 2,637,738 and Ryan, et al., J. Am. Chem. Soc., 82, 3601 (1960), respectively. Diarylamines such as diphenyl amine and N,N'-diphenyl-p-phenylenediamine have been shown to function as promoters for the reaction between trichlorosilane and allyl chloride See U.S. Pat. No. 3,925,434. Unbranched tertiary amines such as tributylamine have also been used for the reaction between allyl chloride and trichlorosilane. See German Pat. No. 1,156,073. Other examples of the use of unbranched tertiary alkyl and mixed alkyl/aryl amines have been described in Chemical Abstract 111:78085m.

It would be desirable to have improved promoters for platinum-catalyzed hydrosilylation reactions, to provide advantages such as faster reactions, reduced side reactions, lower Pt usage, and/or superior product yields and quality. Such promoters are the subject of the present invention.

SUMMARY

The present invention provides a process for carrying out a platinum catalyzed hydrosilylation reaction between an SiH-containing material and a terminal olefin, comprising:

heating said SiH-containing material and said olefin in the presence of a platinum catalyst and a promoter, said promoter comprising:

a hindered amine or phosphine, or acid salt thereof, containing at least 6 carbon atoms and having the formula

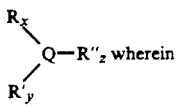

Q is N or P;

when Q is N, R is H, alkyl of 1-18 carbon atoms, nonterminal alkenyl of 4-18 carbon atoms, arylalkyl of 7-25 carbon atoms, or a derivative thereof;

when Q is P, R is alkyl of 1-18 carbon atoms, nonterminal alkenyl of 4-18 carbon atoms, arylalkyl of 7-25 carbon atoms, or a derivative thereof;

x is 0 or 1;

R' is alkyl of 1-18 carbon atoms, nonterminal alkenyl of 4-18 carbon atoms, arylalkyl of 7-25 carbon atoms, or a derivative thereof;

y is 0, 1, or 2;

R" is a branched group having a 2° or 3° carbon atom bonded directly to Q, and is alkyl of 3-18 carbon atoms, nonterminal alkenyl of 4-18 carbon atoms, arylalkyl of 7-25 carbon atoms, or a derivative thereof;

z is 1, 2, or 3 and z=3-x-y; and two R' groups, two R" groups, or one R' and one R" may be taken together to constitute a divalent moiety forming a 5-7 membered ring containing a Q atom.

DETAILED DESCRIPTION

As set forth in the Summary above, the present invention involves the use of sterically hindered secondary or tertiary amines or phosphines, or their acid salts, as promoters for platinum catalyzed hydrosilylation reactions.

Those skilled in the art will also recognize that certain derivatives of the promoters of the invention may be formed in situ in hydrosilylation reactions involving chlorosilanes, a silyl group replacing an active hydrogen atom, and that such derivatives might also be employed directly. Examples of such derivatives are materials in which a silyl group is attached to the Q atom or to an oxygen atom which initially carried a hydrogen.

The SiH-containing material employed in the process of the invention may be any of the SiH-containing molecules known to the art. Typically, these will be silanes or siloxanes which are known to serve as reactants in the present state-of-the-art hydrosilylation reactions. Such materials and methods for their preparation are well known. See, for example US Pat. No. No. 3,562,786.

Similarly, the olefins employed in the process of the invention are any of the alpha olefins known to the art for use in present state-of-the-art hydrosilylation reactions. They can also be olefins which under the reaction conditions isomerize to alpha olefins. Certain dienes and carbynes should also serve. These materials and methods for their preparation are all well known to the art.

Preferred olefins for preparation of polysiloxane-polyether copolymers for rigid polyurethane foam applications are allyl started polyethers containing at least 50% oxyethylene units and at least one hydroxyl group, and having molecular weights of at least 300.

The hindered amines are preferred over the hindered phosphines for purposes of the invention.

As employed in this application, the term "alkyl" in the definitions of R and R' includes straight and branched alkyl groups as well as cycloalkyl groups containing 5-18 carbon atoms. Examples of suitable alkyl groups are methyl, ethyl, isopropyl, t-butyl, cyclohexyl, etc.

The term "nonterminal alkenyl" includes straight chain, branched, and ring-containing groups possessing a double bond. Examples of such materials are cyclohexenyl, $C_2H_5-CH=C(CH_3)CH_2-$, $C_2H_5-CH=CH-CH_2-$, etc.

The term "arylalkyl" refers to aryl-substituted alkyl groups such as benzyl, 4-octylbenzyl, 2-phenylethyl, 2-phenylpropyl isomers, etc.

R is preferably a branched alkyl group of 3 to 4 carbon atoms when only one R" group is present. Examples are the isopropyl and tertiary butyl groups. However, when the promoter contains 2 R" groups or 1 R" group and 1 branched R' group, branching of R is less critical and promoters in which R is simple alkyl or H are still highly effective.

R' is preferably an alkyl group of 1-6 carbon atoms, and most preferably a branched alkyl group containing 3-6 carbon atoms. Examples of such groups are the isopropyl, tertiary butyl, isobutyl, cyclopentyl, and cyclohexyl groups.

R" is a branched alkyl group preferably containing 3-8 carbon atoms, and most preferably contains 4-6 carbon atoms. Examples are isopropyl, 2-butyl, tertiary butyl, 1-ethyloctyl, cyclohexyl, etc.

The number of R" groups in the promoter is preferably 2 or 3. Furthermore, preferred promoter materials possess at least one 3° carbon atom on the central Q atom, and possess at least 8 carbon atoms in total. Most preferably, the promoters contain at least 2 tertiary carbon atoms on the central Q atom, and contain at least 8 carbon atoms in total.

A preferred embodiment of the promoter of the invention contains 2 R" groups or 1 R" and 1 R' group, joined together to form a 5-7 membered ring containing the Q atom.

Examples of such promoters are the following:

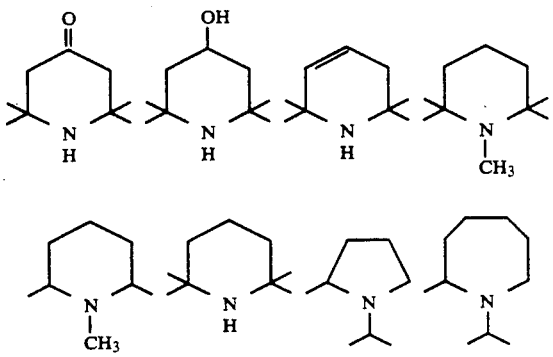

Derivatives of the R, R', and R" groups are moieties such as the keto-, hydroxyl-, cyano-, alkoxyl-, and ester-substituted materials. In addition, the promoter materials may contain two Q atoms, and in this case, the portion of the molecule containing one of the Q atoms may be considered as a substituent on the rest of the molecule, forming a derivative thereof. An example of such a promoter is N,N,N',N'-tetraisopropylethylenediamine, in which one half of the molecule may be considered to be a substituent or derivative of an R group attached to the N atom of the other half.

A keto functionality would typically be present in the promoter as a consequence of the synthetic route by which it was made, or would be introduced deliberately to provide a site for derivatization.

Examples of ketone-containing promoters are the following:

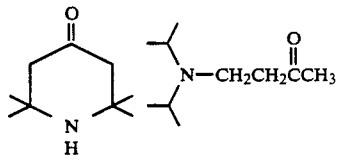

Hydroxyl-substituted derivatives of the R, R', and R" groups are prepared by reactions such as reduction of a keto functionality present in the promoter, or by ethoxylation or propoxylation of a primary or secondary amine. An example of the former is the preparation of 2,2,6,6-tetramethyl-4-piperidinol by reduction of the keto group of commercially available 2,2,6,6-tetramethyl-4-piperidinone, and examples of the latter are >N—CH$_2$CH$_2$OH and >N—CH$_2$CH(CH$_3$)OH, derived from the corresponding amine and either ethylene oxide or propylene oxide.

Cyano functionalities would typically be introduced during synthesis of the promoter by Michael addition of a primary or secondary amine to acrylonitrile, or by reaction of cyanide with an appropriate alkyl halide or derivative of a hydroxyl group.

By alkoxyl-substituted derivatives of R, R and R" are meant simple alkoxyl groups such as methoxy, ethoxy, propoxy, butoxy, benzyloxy, etc., which may be prepared by reaction of a hydroxyl group with an alkyl- or benzyl- halide in the presence of a base, and also more complex ethers such as are produced by reaction of a hydroxyl group and ethylene oxide and/or propylene oxide to form a polyether unit. An example of the latter is the group —O(C$_2$H$_4$O)$_n$(C$_3$H$_6$O)$_m$H, derived from reaction of a hydroxyl group with a mixture of ethylene and propylene oxides.

By ester-substituted derivatives of the R, R', and R" groups are meant acyl derivatives such as an acetoxy group formed by reaction of a hydroxyl group with acetic anhydride, ester-containing groups such as acrylates and methacrylates produced by Michael addition of a primary or secondary amino nitrogen across the olefinic double bond of an acrylic or methacrylic ester, and ester-containing groups produced by reaction of an appropriate amine with an alpha-halo ester. Examples of such materials are R'$_2$NCH$_2$CH$_2$CO$_2$Et and R'$_2$NCH(CH$_3$)CO$_2$Et.

When the promoter is a ring structure containing the Q atom, this ring may bear one or more substituents such as keto, cyano, alkoxyl, hydroxyl, or ester groups. In some cases these groups are present as a consequence of the synthetic route used in making the promoter. The keto functionality is an example of such a group. Certain commercially available materials which have promoter activity have groups such as hydroxyl present to permit derivatization, and these groups may or may not affect the utility of the promoter in hydrosilylation reactions.

Examples of hindered amine promoters which find utility in this invention are:
   a) 2,2,6,6-tetramethyl-4-piperidinol,
   b) 2,2,6,6-tetramethylpiperidine,
   c) 1,2,2,6,6-pentamethyl-4-piperidinol,
   d) 1,2,2,6,6-pentamethyl-piperidine,
   e) benzyldiisopropylamine,
   f) di-t-butylamine,
   g) dicyclohexylamine,
   h) N,N,N',N'-tetraisopropylethylenediamine,
   i) N-isopropylpiperidine,
   j) 2,2,6,6-tetramethyl-4-(2-hydroxyethoxy)-, piperidine, and
   k) 2,2,6,6-tetramethyl-4-piperidone.

Examples of hindered phosphine promoters which find utility in the invention are:
   a) tri-tert-butylphosphine,
   b) benzyldiisopropylphosphine,
   c) ethyl di-tert-butylphosphine, and
   d) di-tert-butylpentylphosphine.

A number of the hindered amine promoters of the present invention are commercially available, specifically, items a, b, d, f, g, and k of the above list. Others may be synthesized according to methods well known to those skilled in the art such as ammonolysis of halides, reductive amination, and Michael addition of amines to olefins. See, for example, the following references: "Organic Chemistry" by Morrison and Boyd, published by Allyn and Bacon, Inc., (1973); Advanced Organic Chemistry by March, John Wiley and Sons (1985)

Examples of these reactions for preparation of the promoters of the invention are

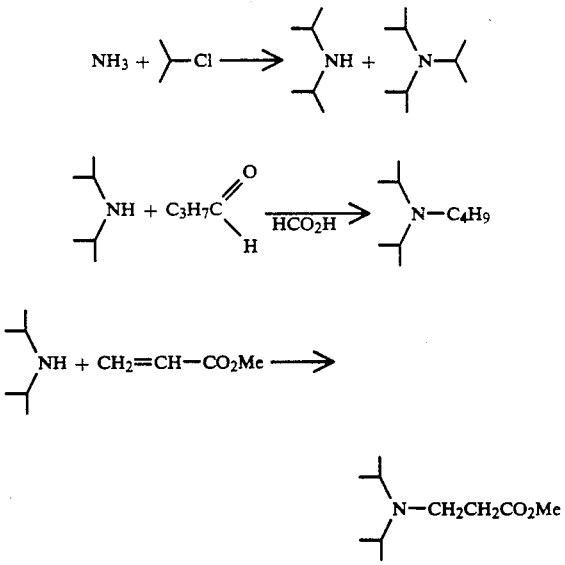

Similarly, the synthesis of the hindered phosphines is known to those skilled in the art. Phosphines can be prepared by a variety of methods, generally starting with phosphine, phosphorous trichloride, or white phosphorous. See, for example, G. M. Kosolapoff, Organophosphorous Compounds, John Wiley and Sons, Inc., New York, New York, pp 10–41 (1950). Some specific reactions are the reaction between an alkyl halide and a metal phosphide, and the reaction between a Grignard reagent and phosphorous trichloride. See, for example, J. R. vanWazer, "Phosphorous and its Compounds", Interscience Publishers, Inc., New York, New York, Vol.1, pp 193–5 (1958).

By way of example, the preparation of tri-tert-butyl-phosphine is described in Chem. Ber., 100(2), 692-3 (1967). Tertiary butyl magnesium chloride is first prepared from magnesium metal and t-butyl chloride, then this is allowed to react with $PCl_3$ to form di-tert-butyl-chlorophosphine. This product is then treated with tert-butyl lithium to yield tri-tert-butyl phosphine.

The improved hydrosilylation process of the invention is conducted in the same manner as the prior art hydrosilylation processes, with the addition of the hindered amine or phosphine promoters. When the reaction is not highly exothermic, the reagents are mixed and heated at 35°-100° C., typically 70°-90 ° C., and then the catalyst is added and heating continued until the reaction is complete. With highly exothermic reactions, a mixture of the catalyst and either the SiH fluid or the olefin is prepared, and the olefin or the SiH fluid is then added over time, with cooling as necessary to control the reaction. The promoter, which is employed at a level of 10 ppm to 10% by weight of the reaction mixture, preferably 10 ppm to 1%, may be added to the reaction mixture at the point the reagents are combined, or alternatively, the promoter and the catalyst may be premixed and added to the hydrosilylation reaction mixture as a single ingredient. Thus, a composition for use in a hydrosilylation reaction comprises a catalytically active platinum-containing material and a promoter as defined above.

GLOSSARY

As employed in this application, the following abbreviations are defined as indicated below:

CPA stands for chloroplatinic acid hexahydrate, generally employed as a 10% by weight solution in ethanol unless otherwise indicated.

D stands for a dimethylsiloxy unit, having the formula $O_{\frac{1}{2}}Si(Me)_2O_{\frac{1}{2}}$.

D' stands for a hydridomethylsiloxy unit having the formula $O_{\frac{1}{2}}Si(H)(Me)O_{\frac{1}{2}}$.

$D_4$ stands for octamethylcyclotetrasiloxane.

L-31 is a precursor of D' units, having the formula $Me_3SiO(Si(H)(Me)O)_xSiOMe_3$.

M stands for the trimethylsiloxy unit, having the formula, $Me_3SiO_{1/8}$.

MM stands for hexamethyldisiloxane.

NaProp. stands for sodium propionate.

NaAsc. stands for sodium ascorbate.

P-1 stands for allyl-started polyether based on ethylene oxide, and has a molecular weight of approximately 350.

P-2 stands for allyl-started polyether based on ethylene oxide, having a molecular weight of approximately 550.

P-3 stands for allyl-started polyether based on ethylene oxide and propylene oxide, having a molecular weight of approximately 750.

PMP stands for 1,2,2,6,6-pentamethylpiperidine, available from Aldrich.

Pt-Co color test employed was ASTM Standard Test Method D-1209.

S-1 stands for an SiH fluid, $MD_xD'_yM$ prepared from the reagents listed in Table 1.

S-2 stands for an SiH fluid $MD_xD'_yM$ prepared using the reagents of Table 1.

TBA stands for tributylamine.

TBP stands for tri(tert-butyl)phosphine.

TEA stands for triethylamine.

TEDA stands for triethylene diamine, a cage structure containing two nonhindered nitrogen atoms.

TMHP stands for 2,2,6,6-tetramethyl-4-hydroxy piperidine, available from Ciba-Geigy.

TMP stands for 2,2,6,6-tetramethylpiperidine.

The turbidity test employed as a measure of water solubility was ASTM Standard Test Method D-1889.

EXPERIMENTAL

Preparation of SiH siloxanes ($MD_xD'_yM$)

To a 500 ml round bottom flask equipped with a glass stirring rod with a Teflon ® blade and driven by a stirrer motor were charged the desired amounts of hexamethyldisiloxane (MM), octamethylcyclotetrasiloxane ($D_4$), L-31, and 2% by weight of sulfuric acid, based on the total weight of the foregoing reagents. The flask was stirred for 24 hours at ambient temperature. The flask contents were then slowly neutralized with an excess of dampened sodium bicarbonate. The product was treated with 0.5 wt. % activated carbon and pressure filtered to give a colorless liquid which was characterized as to SiH content and viscosity. SiH content was determined by measuring the amount of hydrogen produced in a reaction of a sample with an ethanol solution of KOH in a fermentation tube. The charges used for the preparations of siloxane fluids S-1 and S-2 are shown in Table 1, as percents of the total amount of the reactants.

TABLE 1

| Fluid Designation | D/D' Ratio | Starting Materials | | |
|---|---|---|---|---|
| | | MM (%) | Cyclic $D_4$ (%) | L-31 (%) |
| S-1 | 2.6 | 8.6 | 67.3 | 22.1 |
| S-2 | 3.4 | 4.7 | 74.6 | 18.7 |

PREPARATION OF $MD_xD''_yM$ Copolymers

A 500ml round bottom flask fitted with a glass stirring rod having a Teflon ® blade and driven by a stirrer motor was charged with the desired polyether or blend of polyethers (using a 30 mole percent excess), $MD_xD'_yM$ fluid, and promoter/buffer at the levels specified below. The flask was equipped with a thermometer, condenser, and a nitrogen sparging tube. The mixture was heated to the specified initial temperature with a slow nitrogen sparge and then a solution of 10% chloroplatinic acid hexahydrate in ethanol was added. An exotherm of several degrees and a change from "cloudy" to "clear" were noted. Samples were analyzed for SiH content at regular intervals until at least 99% of the original SiH had been consumed. The residual SiH was determined by measuring the amount of hydrogen produced in a reaction of an aliquot with an ethanol solution of KOH in a fermentation tube. The material was then neutralized with sodium bicarbonate and then pressure filtered.

Trials of Various Buffer/Promoters in a Hydrosilylation Reaction (Experiments 1–8)

A number of buffer/promoter materials were employed in a hydrosilylation reaction carried out as described above for the preparation of the $MD_xD''_yM$ copolymers. Reactants were siloxane S-1 (70.8g) and polyether P-1 (129.28g, 30% in excess), and the catalyst was CPA (10% solution in ethanol). 1000 ppm of buffer/promoter were used in each run employing such material. Initial temperature in each case was 85° C. 25 ppm of Pt were employed in each experiment except for No. 4, where 140 ppm of Pt were required. The data are shown in Table 2.

TABLE 2

Effect of Buffer/Promoter On Hydrogen Formation During Hydrosilylation Reactions

| | Experiment No. | | |
|---|---|---|---|
| | 1 | 2 | 3 |
| Buffer/Promoter | none | NaProp. | NaAsc. |
| Time to Clearing (min) | 2 | 8 | 4 |
| Total Time (min) | 4 | 12 | 12 |
| Maximum Temperature (°C.)[a] | 143 | 126 | 136 |
| Viscosity (cSt)[b] | gelled | 333 | 2215 |
| 5% H$_2$O Solubility (NTU)[c] | — | 100 | 40 |
| H$_2$ evolved (ml)[d] | 250 | 126 | 204 |

| | Experiment No. | | |
|---|---|---|---|
| | 4 | 5 | 6 |
| Buffer/Promoter | 2,6-Lutidine | TEDA | TBA |
| Time to Clearing (min) | 92 | 6 | 3 |
| Total Time (min) | 92 | 11 | 7 |
| Maximum Temperature (°C.)[a] | 88 | 129 | 146 |
| Viscosity (cSt)[b] | gelled | 606 | 360 |
| 5% H$_2$O Solubility (NTU)[c] | — | 180 | 32 |
| H$_2$ Evolved (ml)[d] | >500 | 280 | 186 |

| | Experiment No. | |
|---|---|---|
| | 7 | 8 |
| Buffer/Promoter | TEA | TMHP |
| Time to Clearing (min) | 3 | 2 |
| Total Time (min) | 7 | 7 |
| Maximum Temperature (°C.)[a] | 147 | 142 |
| Viscosity (cSt)[b] | 347 | 331 |
| 5% H$_2$O Solubility (NTU)[c] | 48 | 20 |
| H$_2$ Evolved (ml)[d] | 176 | 105 |

[a]Maximum temperature resulting from exotherm
[b]Kinematic viscosity determined by ASTM procedure D-445
[c]Nephelometric Turbidity Units, measured on 5% copolymer in water by ASTM procedure D-1889
[d]Hydrogen evolved during the reaction was measured by displacement of water in an inverted graduated cylinder placed in a trough of water.

Table 2 shows the impact of buffers/ promoters on the hydrosilylation reaction rate and the viscosity and water solubility of siliconepolyether copolymers which are derived by the hydrosilylation reaction of a hydroxyl endblocked allyl-started polyether and a trimethylsiloxy endblocked methylhydrogen/dimethyl polysiloxane fluid. To prepare such structures with a high degree of consistency it is desirable to avoid side reactions such as crosslinking, which can alter the solubility properties of the product. The two major crosslinking reactions which must be controlled result from dehydrocondensation and acetal formation.

Dehydrocondensation refers to the reaction of SiH units of the siloxane with proton donors such as water or hydroxyl groups on unreacted or grafted polyethers in the system. The reaction with water produces hydrogen and a silanol group which can in turn react with a silanol or an SiH unit of another siloxane molecule to produce a crosslink. The reaction with a hydroxyl group of a polyether also produces hydrogen, as well as a crosslink if the polyether is or becomes attached to another siloxane molecule. Crosslinking affects the molecular weight and the silicone/polyether ratio of the product siloxane-polyether, thereby affecting its properties.

Acetal formation is a consequence of isomerization of the terminal allyl group of an allyl polyether to yield a propenyl polyether which does not undergo hydrosilylation but can react with the hydroxyl group of a polyether bound to a siloxane to yield a noncrosslinked acetal, which in turn can react further by transacetylization with another such molecule to produce crosslinking. Acetal chemistry generally takes place under acid conditions such as those obtained during chloroplatinic acid catalyzed hydrosilylations carried out in the absence of a buffer. It is expected to be minimal in amine-promoted hydrosilylation reactions.

Experiments 1–7 are comparative tests of the various buffer/promoter materials, relative to experiment 8, which employs a promoter of the present invention. Examples 1, 3, 4, and 5 exhibit abnormally high viscosities or gelling, as well as high to very high hydrogen evolution, indicating the occurance of crosslinking via dehydrocondensation and/or acetal formation. The volume of hydrogen gas generated during the reaction, which is a measure of the extent of the dehydrocondensation reaction which is to be avoided, shows that the compound of the invention, TMHP, causes less dehydrocondensation than any of the other materials tested, and substantially less than any of the other amines.

Effect of Temperature on TMHP Promoted Hydrosilylation Reactions (Experiments 9–15)

Hydrosilylation reactions promoted with TMHP were compared with reactions promoted with sodium propionate. The reactions were conducted as discussed above in the section on Preparation of MD$_x$D"$_y$M copolymers. For experiments 9–13, 78.1 g of S-2 and 121.9 g of P-1 were employed. For experiments 14–15, 54.8 g of S-1 and 145.2 g of P-2 were employed. 1000 ppm of buffer/promoter and 25 ppm of Pt catalyst were employed in each case. Results are shown in Table 3.

Effect of Temperature on Solventless Hydrosilylation Reactions Using TMHP Promoter

| | Experiment No. | | | |
|---|---|---|---|---|
| | 9 | 10 | 11 | 12 |
| Siloxane | S-2 | S-2 | S-2 | S-2 |
| Polyether[a] | P-1 | P-1 | P-1 | P-1 |
| Buffer/Promoter | TMHP | TMHP | TMHP | TMHP |
| Initial Temp. (°C.) | 85 | 70 | 60 | 50 |
| Time to Clearing (min) | 1 | 3 | 5.5 | 30 |
| Total Time (min) | 13 | 23 | 18 | 43 |

| | Experiment No. | | |
|---|---|---|---|
| | 13 | 14 | 15 |
| Siloxane | S-2 | S-1 | S-1 |
| Polyether[a] | P-1 | P-2 | P-2 |
| Buffer/Promoter | NaProp. | TMHP | NaProp. |
| Initial Temp. (°C.) | 75 | 75 | 85 |
| Time to Clearing (min) | NA | 6 | 36 |
| Total Time (min) | >60 | — | 43[b] |

[a]employed 30% in excess
[b]Still heterogeneous after 1 hr. Reaction mixture would have been homogeneous at approximately 70% completion.

Experiments 9–12 of Table 3 shows that the hindered amine TMHP allowed the hydrosilylation reaction to initiate at temperatures as low as 50° C. and go to completion without additional external heating, and Examples 13–15 show that in reactions initiated at higher temperatures, TMHP is much more effective than the prior art material sodium propionate. It is common to initiate hydrosilylation reactions of allyl polyethers and SiH fluids at temperatures between 75° and 85° C. With relatively insoluble reactants such as those employed here, it is sometimes necessary to raise the temperature to 90°-95° C. to facilitate the reaction. In contrast to the TMHP promoter of the present invention, the sodium propionate promoter of the prior art functioned substantially less well, as shown by the fact that the reaction mixture was still heterogeneous after one hour's reaction time, while the TMHP promoter showed a clearing time of minutes.

Comparison of Sodium Propionate and TMHP As Promoters in Hydrosilylation Reactions (Experiments 16–23)

Four sets of solventless hydrosilylation reactions were conducted at 85° C. in the presence of 25 ppm of Pt, with different combinations of SiH fluid and allyl polyether. In experiments 16 and 17, 78.1 g of S-1 and 121.9 g of P-1 were used. In experiments 18 and 19, 54.8 g of S-1 and 145.2 g of P-2 were used. In experiments 20 and 21, 50.7 g of S-2 and 149.3 g of P-3 were used. In experiments 22 and 23, 78.1 g of S-2 and 121.9 g of P-1 were used. Each hydrosilylation reaction was run with sodium propionate and with TMHP as promoter, to permit comparisons of these materials as promoters. Results are given in Table 4.

TABLE 4

Reaction Rate Enhancement with Promoters in Hydrosilylation of Uncapped Polyethers

| | Experiment No. | | | |
|---|---|---|---|---|
| | 16 | 17 | 18 | 19 |
| Siloxane | S-1 | S-1 | S-1 | S-1 |
| Polyether | P-1 | P-1 | P-2 | P-2 |
| Buffer/Promoter | NaProp. | TMHP | NaProp. | TMHP |
| Time to Clearing (min)[b] | 8 | 2 | 36 | 3 |
| Total Time (min)[c] | 12 | 7 | 43 | 12 |

| | Experiment No. | | | |
|---|---|---|---|---|
| | 20[a] | 21 | 22 | 23 |
| Siloxane | S-2 | S-2 | S-2 | S-2 |
| Polyether | P-3 | P-3 | P-1 | P-1 |
| Buffer/Promoter | NaProp. | TMHP | NaProp. | TMHP |
| Time to Clearing (min)[b] | 33 | 3 | 12 | 1 |
| Total Time (min)[c] | 44 | 7 | 52 | 13 |

[a]50 ppm Pt. required
[b]Clear time is approximately 70% completion
[c]Total time is time to completion (SiH < 0.1 ml H$_2$/g)

Table 4 compares the state of the art technology, i.e., platinum catalyzed hydrosilylations using carboxylate salt buffers, against the highly hindered amine TMHP. It can be seen that in every case the reactions employing the hindered amine reached the clear point first and went to completion at a much faster rate. In the case of experiment 20 the control required 50 ppm of platinum catalyst while the TMHP promoted reaction went to completion in 7 minutes with the single 25 ppm platinum catalyst charge.

Improvement in the Water Solubility of Copolymers Prepared with Hindered Amines

A number of hydrosilylation reactions were conducted using siloxane S-1 and either polyether P-1 or polyether P-2, and were promoted by various amines or carboxylate salts as shown in Table 5. Again, the hydrosilylation reactions were conducted as discussed above in the paragraph on Preparation of MD$_x$D"$_y$M copolymers. Copolymers containing S-1 and P-1. Copolymers containing S-1 and P2 were prepared using 54.8 g of S-1 and 145.2 g of P-2. In each case, 1000 ppm of buffer/promoter and 25 ppm of Pt catalyst were employed. The water solubility of the resultant copolymers was determined turbidimetrically. Results are shown in Table 5.

TABLE 5

Water Solubility of Silicone-Polyether Copolymers Prepared With Various Promoters

| Polyether | Buffer/Promoter | Turbidity (NTU)[c] |
|---|---|---|
| P-1 | NaProp. | 100 |
| P-1 | TEA | 48 |
| P-1 | TMHP[a] | 20 |
| P-1 | TMP[a] | 24 |
| P-2 | NaProp. | >200 |
| P-2 | TMHP[a] | 34 |
| P-2 | PMP[a] | 40 |
| P-2 | TBA | 134 |
| P-2 | TMHP/CPA[a,b] | 19 |

[a]Promoter of the invention
[b]TMHP promoter premixed with CPA solution.
[c]Lower numbers indicate better water solubility.

For certain applications it is desirable that the siloxane-polyether copolymer be as highly water soluble as possible. The results shown in Table 5 demonstrate that the hindered amines of the present invention provide products having substantially better water solubilities than are produced using carboxylate salts or the nonhindered amines of the prior art. It was also noted in these experiments that the hindered secondary or tertiary amines of the present invention gave the fastest reaction times, as indicated by the time required for the reaction mixture to become homogeneous. It also appears that premixing the TMHP and catalyst can be advantageous.

Hydrosilylations Using TMHP and Low Platinum Levels (Experiments 24–27)

Several hydrosilylation reaction were conducted according to the procedure presented above for the preparation of MD$_x$D"$_y$M copolymers, except that instead of the 25 ppm of platinum generally used when conducting a hydrosilylation reaction using the reactants shown in Tables 1, 2, or 3 in which a compatibilizing solvent is not employed and state of the art buffers/promoters such as sodium or potassium carboxylates are used, platinum levels of between 2 and 5 ppm were used. In experiments 24 and 25, 70.8 g of S-1 and 129.2 g of P-1 were used. In experiments 26 and 27, 78.1 g of S-2 and 121.9 g of P-1 were used. TMHP was employed at 1000 ppm. Results are shown in Table 6.

TABLE 6

Hydrosilylation using TMHP and Low Pt Levels

| | Experiment No. | | | |
|---|---|---|---|---|
| | 24 | 25 | 26 | 27 |
| Siloxane | S-1 | S-1 | S-2 | S-2 |
| Polyether[a] | P-1 | P-1 | P-1 | P-1 |
| Initial Temp. (°C.) | 80 | 75 | 70 | 80 |
| Amount Pt (ppm) | 3 | 3* | 5 | 2 |
| Clear Time (min) | 12 | 39 | 22 | 19 |
| Total Time (min) | 20 | 54 | 31 | 74 |
| Color (Pt-Co) | 20–30 | 20 | — | — |

[a]employed 30% in excess, as usual
*Catalyst added as 3% CPA in ethanol. Others were 10% CPA solutions.

Typically, when hydrosilylation reactions are conducted with 10 ppm of platinum or less, the platinum is likely to deactivate before the reaction is complete. This deactivated platinum catalyst can adversely affect the turnover number of any fresh catalyst that is added. Thus, the total catalyst required can become higher than if an adequate amount of catalyst was introduced originally. Table 6 shows that unusually low levels of platinum catalysts may be used when the hindered amine promoters/buffers of the present invention are employed. No evidence of catalyst deactivation was seen in these experiments. The product copolymers were tested as rigid foam surfactants and showed normal performance.

It is common for siloxane-polyether copolymers prepared via hydrosilylation to have a brown or gray cast due to elemental particles of spent platinum catalyst present in the product. For reactions conducted with 15 ppm Pt and no promoter, the Pt-Co color test typically gives a reading of 150-300 Experiments 24 and 25, where the color of the product was analytically determined, showed unusually low color. This is a highly desirable feature in some applications such as cosmetics.

Hydrosilylation of Allyl Cyanide (Experiments 28 and 29)

A hydrosilylation reaction was conducted using allyl cyanide and trichlorosilane as the reactants. The procedure employed was generally that discussed above for the preparation of the $MD_xD''_yM$ copolymers, with the exceptions that instead of an allyl polyether, allyl cyanide was employed, and the trichlorosilane was fed into the reaction at a rate sufficient to keep the reaction temperature in the range 100°-105° C. Twenty ppm of platinum were employed as the catalyst. Additionally, as allyl cyanide is a particularly difficult olefin to hydrosilylate because of its ability to severely inhibit the platinum catalyst, acetic acid was used as a catalyst modifier in Experiment 28 as is typically done in these sorts of reactions.

A 250 ml 4-necked round bottom flask was equipped with a magnetic stirrer, Friedrick water condenser, 125 ml addition funnel, thermometer, temperature controller, septum, and a nitrogen inlet. The flask was charged with 35.5 g of allyl cyanide and either 1.88 g of acetic acid (experiment 28) or 0.0042 g (40 ppm based on total charge) of 2,2,6,6-tetramethyl-4-piperidinol (experiment 29), and the addition funnel was charged with 71 g of $HSiCl_3$. The flask was heated to 100° C. then about 10 drops of $HSiCl_3$ were added, followed by 57 microliters of a 10% solution of chloroplatinic acid (20 ppm Pt based on the total charge). No initial exotherm was noted. A dropwise addition of $HSiCl_3$ was begun and the flask temperature was controlled at 100°-105° C. by a combination of external temperature control and $HSiCl_3$ addition rate. The $HSiCl_3$ addition was continued dropwise with some external heating until the $HSiCl_3$ addition was complete. Some reflux was noted toward the end of the reaction, at which time the $HSiCl_3$ addition was temporarily halted. After the complete $HSiCl_3$ addition, the reaction mixture was held at 100° C. for 1 hour. Gas chromatographic analytical results are provided in Table 7.

TABLE 7

| | Experiment No. | |
|---|---|---|
| | 28 | 29 |
| Hydrosilylation of Allyl Cyanide | | |
| Reagents: | | |
| Allyl Cyanide (g) | 34.2 | 35.5 |
| $HSiCl_3$ (g) | 67.6* | 71.0 |
| Promoter | Acetic Acid | TMHP |
| Amount Promoter (g) | 1.88 | 0.0042 |
| Conditions & Results after 50% chlorosilane Addition | | |
| $HSiCl_3$ feed rate (cc/min) | 0.48 | 0.84 |
| Reaction Time (min) | 52 | 31 |
| Mixture Composition: | | |

TABLE 7-continued

| | Experiment No. | |
|---|---|---|
| | 28 | 29 |
| $HSiCl_3$ (%) | 1.41 | 0.03 |
| Allyl Cyanide (%) | 39.9 | 32.8 |
| Product (%) | 57.4 | 65.7 |
| Conditions & Results at 100% Chlorosilane Addition | | |
| $HSiCl_3$ feed rate (cc/min) | 0.25 | 0.55 |
| Reaction Time (hr) | 3.7 | 2.6 |
| Mixture Composition | | |
| $HSiCl_3$ (%) | 10.9* | 10.9 |
| Allyl Cyanide (%) | 17.3 | 12.9 |
| Product (%) | 69.0 | 75.2 |

*2.7 g of $HSiCl_3$ not added due to continued refluxing of unreacted $HSiCl_3$.

Table 7 shows that using a low level of TMHP in the hydrosilylation reaction gave a faster reaction and a higher yield of the product than was achieved in the control reaction with acetic acid.

Hydrosilylation of Allyl Chloride With Trichlorosilane (Experiments 30-33)

To a 500 ml four necked flask equipped with an addition funnel, stirrer, reflux condenser, and thermometer, was added 76.5 grams of allyl chloride and 0.068 ml of a ten percent CPA solution (11 ppm based on the total batch weight. The amount of promoter shown in the table below was also added to the reaction flask. The flask was heated to approximately 45° C. and a total of 156 gms of trichlorosilane was then added slowly to the flask via the addition funnel. The results of these reactions are shown in Table 8 below.

TABLE 8

| Hydrosilylation using TMHP and Low Pt Levels | | | | |
|---|---|---|---|---|
| | Experiment No. | | | |
| | 30 | 31 | 32 | 33 |
| Promoter | None | TMP[a] | TMHP[b] | TBP[c] |
| Silane Addition Time (hr) | 2.06 | 1.78 | 2.0 | 3 |
| Temperature Range (°C.) | 38-42 | 48-67 | 45-78 | 47-62 |
| Residual $HSiCl_3$ (%) | 48.8 | 5.0 | 4.2 | 4.7 |
| Residual allyl chloride (%) | 28.1 | 0.9 | 0.04 | 0.03 |
| Silicon Tetrachloride (%) | 7.9 | 17.9 | 17.9 | 21.2 |
| Propyl Trichlorosilane (%) | 0.07 | 7.0 | 6.4 | 3.18 |
| γ-chloro propyltri-chlorosilane (%) | 13.5 | 68.0 | 70.6 | 65.1 |
| "Heavies" (%) | 0.3 | 0.3 | 0.6 | 4.6 |

[a]35 ppm based on total weight of reactants
[b]20 ppm based on total weight of reactants
[c]26 ppm based on total weight of reactants Hydrosilylation of allyl chloride with trichlorosilane to produce γ-chloropropyltrichlorosilane has historically been characterized by major amounts of side reactions, the most important of which is the formation of silicon tetrachloride and propylene. The propylene can then react with trichlorosilane to produce propyltrichlorosilane. Table 8 shows in Experiment 30 that the reaction conducted in the absence of a promoter is sluggish and produces only a very low yield of the desired product. This control reaction also exhibits the worst ratio of desired product to undesired byproduct. Reactions 31-33, in which promoters of the present invention were employed, proceeded much faster than the control and afforded much higher yields of the desired product. It is also apparent that the best ratio of the desired product to the undesired byproducts is given in the reaction using TMHP as the promoter, with TMP and TBP promoters producing somewhat less of the desired product and more byproducts, but nevertheless being far superior to the control reaction.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A process for carrying out a platinum catalyzed hydrosilylation reaction between an SiH-containing material and a terminal olefin, comprising:

heating said SiH-containing material and said olefin in the presence of a platinum catalyst and a promoter, said promoter comprising:

a hindered amine or phosphine, or acid salt thereof, containing at least 6 carbon atoms and having the formula

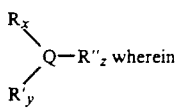

Q is N or P;

when Q is N, R is H, alkyl of 1–18 carbon atoms, nonterminal alkenyl of 4–18 carbon atoms, arylalkyl of 7–25 carbon atoms, or a derivative thereof;

when Q is P, R is alkyl of 1–18 carbon atoms, non-terminal alkenyl of 4–18 carbon atoms, arylalkyl of 7–25 carbon atoms, or a derivative thereof;

x is 0 or 1;

R' is alkyl of 1–18 carbon atoms, nonterminal alkenyl of 4–18 carbon atoms, arylalkyl of 7–25 carbon atoms, or a derivative thereof;

y is 0, 1, or 2;

R" is a branched group having a 2° or 3° carbon atom bonded directly to Q, and is alkyl of 3–18 carbon atoms, nonterminal alkenyl of 4–18 carbon atoms, arylalkyl of 7–25 carbon atoms, or a derivative thereof;

z is 1, 2, or 3 and z=3-x-y; and two R' groups, two R" groups, or one R' and one R" may be taken together to constitute a divalent moiety forming a 5–7 membered ring containing a Q atom.

2. The process of claim 1 wherein the hydrosilylation reaction is carried out in the absence of a solvent.

3. The process of claim 1 wherein the promoter comprises at least two R" groups.

4. The process of claim 1 wherein the promoter comprises a 5–7 membered ring containing a Q atom.

5. The process of claim 1 wherein the SiH-containing material is a polysiloxane or a silane, and the olefin is an alpha olefin.

6. The process of claim 1 wherein said olefin is an allyl started polyether containing at least 50% by weight oxyethylene units and at least one hydroxyl functionality.

7. The process of claim 1 wherein said promoter and the platinum catalyst are premixed before being employed in the hydrosilylation reaction.

8. The process of claim 1 wherein said promoter is 2,2,6,6-tetramethyl-4-piperidinol.

9. The process of claim 1 wherein said promoter is 2,2,6,6-tetramethyl-4-piperidinone.

10. A composition for use in hydrosilylation reactions, comprising:

(a) a catalytically active platinum-containing material; and (b) a promoter as defined in claim 1.

* * * * *